(12) United States Patent
Dannenberg et al.

(10) Patent No.: US 7,183,316 B2
(45) Date of Patent: Feb. 27, 2007

(54) TREATMENT OF HPV CAUSED DISEASES

(75) Inventors: Andrew J. Dannenberg, New York, NY (US); Kotha Subbaramaiah, Flushing, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 27 days.

(21) Appl. No.: 10/096,819

(22) Filed: Mar. 14, 2002

(65) Prior Publication Data

US 2002/0164385 A1 Nov. 7, 2002

Related U.S. Application Data

(60) Provisional application No. 60/288,107, filed on May 3, 2001.

(51) Int. Cl.
*A61K 31/34* (2006.01)
*A61K 31/451* (2006.01)
*A61K 31/38* (2006.01)
*A61K 31/60* (2006.01)

(52) U.S. Cl. .................. 514/473; 514/406; 514/403; 514/471; 514/438; 514/165

(58) Field of Classification Search ........... 514/473, 514/406, 403, 471, 165, 438; 424/9.1, 9.2
See application file for complete search history.

(56) References Cited

U.S. PATENT DOCUMENTS 5,079,262 A * 1/1992 Kennedy .................. 514/561
6,218,373 B1 * 4/2001 Falk et al. ................ 514/54
2001/0010899 A1 8/2001 Robert ..................... 435/5
2003/0004143 A1 * 1/2003 Prior et al. ............... 514/165

FOREIGN PATENT DOCUMENTS

WO WO 98/16227 4/1998

OTHER PUBLICATIONS

Harald zur Hause, Biochimica et Biophysica Acta 1288 (1996) F55-F78.*
Vioxx RN 162011-90-7, Etodolac RN 41340-25-4, Registry copyright 2003 ACS.*
Bauer et al, Pharmacotherapy, A Pathophysiologic Approach, 2nd ed. 1992 at p. 15, 1st para.*
Goodman and Gillman, McGraw-Hill Pub. 10th ed. 2001, p. 707.*
Robinson et al (Laryngoscope, 1999, 109:1137-1141).*
Pentland et al (Carcinogenesis, 1999: 20(10): 1939-1944).*
Mukherjee et al, JAMA, Aug. 22-29, 2001, 286:954-959.*
Carol and Richard Eustic published at ://arthritis.about.com/od/vioxx/a/vioxxrecall.htm, last visited on May 4, 2005, 3/3.*
FDA Statement published on Dec. 17, 2004 obtained from ://Fda.gov/bbs/topics/news/2004/new01144.html, last visited May 4, 2005, 2/2; also Public Health Advisory on NSAIDS available on ://FDA.gov/cder/drug/advisory/nsaids.htm last visited May 4, 2005, 2/2.*
Prior et al, U.S. Appl. No. 60/284,756, filed Apr. 18, 2001.*

* cited by examiner

Primary Examiner—Shengjun Wang
(74) Attorney, Agent, or Firm—Bacon & Thomas, PLLC

(57) ABSTRACT

Human papillomavirus (HPV) protein expression is down-regulated in patients infected with HPV by administration of PPARγ ligand, selective inhibitor of cyclooxygenase-2 (COX-2), diaryl heterocycle, inhibitor of HPV protein from a natural source and/or certain non-steroidal anti-inflammatory drugs.

3 Claims, 1 Drawing Sheet

TREATMENT OF HPV CAUSED DISEASES

CROSS-REFERENCE TO RELATED APPLICATIONS

This application claims the benefit of U.S. Provisional Application No. 60/288,107, filed May 3, 2001.

TECHNICAL FIELD

This invention is directed to downregulating expression of human papillomavirus (HPV) proteins to treat patient infected with HP virus.

BACKGROUND OF THE INVENTION

HPVs have been implicated in causing pathological conditions ranging from anogenital warts to cutaneous warts to cervical cancer.

Anogenital warts have been found to be associated with HPV types 6 and 11. HPV types 1, 2, 4 and 57 have been found to be associated with common cutaneous warts. HPV types 26, 30, 34, 40, 45, 54, 55, 58, 59, 61, 62, 64 and 67 to 70 have also been found in warts and neoplasias. HPV types 16, 18, 31, 33, 35, 39, 41, 42, 43, 44, 45, 51, 52 and 56 have been found to be involved in cervical dysplasia and invasive cervical cancer. Types 16 and 18 have been found to be involved with other kinds of cancer as well Proteins E6 and E7 which are expressed by HPV16 and HPV18 are believed to play a major role in the carcinogenesis.

No treatment has been found to be completely satisfactory for anogenital warts or for inhibiting effects of HPV infection.

SUMMARY OF THE INVENTION

It has been found herein that effects of HPV infection can be inhibited by downregulating the expression of HPV proteins by administering a therapeutically effective amount of an inhibitor of the expression of HPV protein.

An invention herein is directed to a method of downregulating expression of HPV protein in a human patient infected with an HP virus comprising administering to said patient a therapeutically effective amount of an inhibitor of the expression of HPV protein.

The inhibitors of the expression of HPV protein include certain PPARγ ligands, selective inhibitors of cyclooxygenase-2(COX-2), certain diaryl heterocycles, certain inhibitors from natural sources and certain nonsteroidal anti-inflammatory drugs and metabolites thereof, alone or in combination.

The term "HPV protein" is used herein to mean protein expressed by HP virus.

Anogenital and cutaneous warts caused by HPV infection usually can be identified by appearance.

A pap smear is able to detect most cases of cervical dysplasia (precursor to invasive cervical cancer).

An FDA-approved test is now available to determine presence of HPV types that cause cervical cancer (see Modern Drug Discovery, July/August 2000, 57–64).

Any expression of HPV protein is considered pathological.

DETAILED DESCRIPTION

Figure 1:
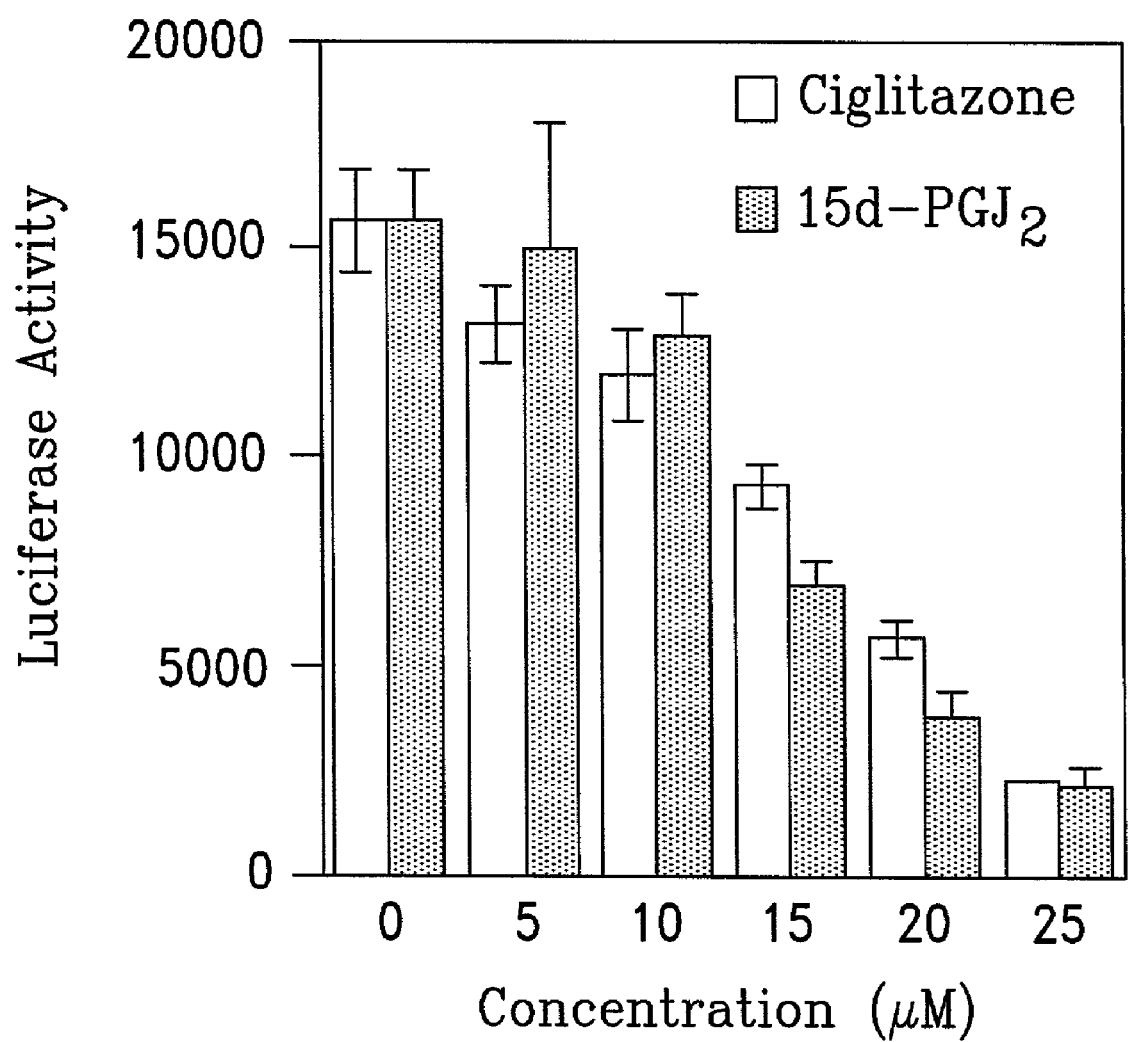
FIG. 1 shows luciferase activity on incubation of recited concentrations of ciglitazone and 15d-PGJ$_2$ with HPV16 upstream regulatory region ligated to a luciferase gene transfected into CaSki cells.

We turn now to the method herein of downregulating expression of HPV protein in a patient infected with an HP virus comprising administering to said patient a therapeutically effective amount of an inhibitor of the expression of HPV protein.

The HP viruses referred to include all HP viruses and comprise types 1, 2, 4, 6, 11, 16, 18, 26, 30, 31, 33, 34, 35, 39, 40, 41, 42, 43, 44, 45, 51, 52, 54, 55, 56, 57, 58, 59, 61, 62, 64, 67, 68, 69 and 70. HPV6 and HPV11are representative of a group of HP viruses characterized as a low risk group and are associated with anogenital warts. HPV 1, 2, 4 and 57 are associated with common cutaneous warts. HPV16 and HPV18 are representative of a group of HP viruses characterized as a high risk group and are associated with cervical intraepithelial neoplasia and invasive cervical cancer.

The pathologic conditions treated by the method herein comprise anogenital and cutaneous warts, cervical intraepithelial neoplasia, anal, perianal, vulvar, penile, skin (squamous carcinoma), and oropharyngeal (20% HPV associated) cancers as well as related premalignant conditions and respiratory papillomas including tumors of the larynx and respiratory epithelium.

The HPV proteins referred to include all proteins encoded by the HP viruses and include the virus encoded proteins associated with high risk HPVs, e.g., HPV16 or HPV18, which have been denoted E6 and E7.

Background examples and working examples herein are directed to administrations to downregulate expression of HPV protein for treatment of anogenital warts, cervical intraepithelial neoplasia, invasive cervical cancer and cutaneous warts, and downregulation of expression of HPV16 E6 and E7, i.e., E6 and E7 protein expressed HPV type 16.

Thus, the invention herein embraces use of the method herein in treating patients infected with HPV6, HPV11, HPV16, and HPV18, e.g., HPV16 and HPV18 mediated cervical cancer and cervical intraepithelial neoplasia and HPV6 or HPV11 mediated genital warts and HPV 1, 2, 4 and 57 mediated cutaneous warts, and downregulating expression of E6 and E7 protein.

We turn now to the inhibitors of expression of HPV protein administered in the method herein.

As indicated above, the inhibitors of expression of HPV protein for administration herein include certain PPARγ ligands, selective inhibitors of COX-2, certain diaryl heterocycles, certain inhibitors from natural sources and certain nonsteroidal anti-inflammatory drugs and metabolites thereof, alone or in combination.

We turn now to the case of inhibitors of expression of HPV protein being PPARγ ligand.

The PPARγ ligands for use as inhibitors of expression of HPV protein in the method herein have a pK$_i$ of at least 4.0 in binding assay using human PPARγ binding domain as generally and particularly described in U.S. Pat. No. 6,219,496, the whole of which is incorporated herein by reference, and include all PPARγ ligands meeting the above general description whether or not they are particularly described in U.S. Pat. No. 6,219,496. The PPARγ ligands for use herein include thiazolidinediones including ciglitazone, pioglitazone, troglitazone and rosiglitazone. The PPARγ ligands for use in the method herein include N-(2-benzoylphenyl)-L-tyrosine derivatives as described in U.S. Pat. No. 6,219,496. Still another PPARγ ligand for use in the method herein is 15-deoxy-Δ12,14-prostaglandin J$_2$ which is sometimes denoted 15-d-PGJ$_2$ or 15d-PGJ$_2$. The dosage of PPARγ ligand for the method of the broad embodiment is a therapeutically effective amount which is an amount resulting in downregulation of expression of HPV protein and in amelioration of the HPV infection and results thereof, e.g., inhibition of cancer cell growth in the case of HPV mediated cancer. In general, the dosage ranges from 0.1 μg/kg to 1,000 mg/kg, per day. For the thiazolidinediones, the dosage preferably ranges from 0.1 to 100 mg/kg, per day. For the N-(2-benzoylphenyl)-L-tyrosine derivatives, the dosage preferably range from 0.01 to 10 mg/kg, per day. For 15-d-PGJ$_2$, the dosage preferably ranges from 0.1 to 100 μg/kg, per day.

We turn now to the case of the inhibitors of expression of HPV protein being selective inhibitors of COX-2. The term "inhibitor of cyclooxygenase-2" is used herein to mean a compound which directly inhibits cyclooxygenase-2 metabolized catalysis of arachidonic. The term includes competitive inhibitors, non-competitive inhibitors, and compounds that form covalent linkages with COX-2. The term "selective inhibitor of cyclooxygenase-2" is used herein to mean compound which selectively inhibits cyclooxygenase-2 in preference to cyclooxygenase-1 and particularly compound for which the ratio of the IC$_{50}$ concentration (concentration inhibiting 50% of activity) for cyclooxygenase-1 to the IC$_{50}$ concentration for cyclooxygenase-2 is greater than 1. Such ratio is readily determined by assaying for cyclooxygenase-2 activity and assaying for cyclooxygenase-1 activity by the methods set forth at column 39, line 55—column 40, line 36 of Talley et al. U.S. Pat. No. 5,633,272, which is incorporated herein by reference, and from the resulting data obtaining a ratio of IC$_{50}$s. Preferably, selective inhibitor of cyclooxygenase-2 is used where the ratio of the IC$_{50}$ concentration for cyclooxygenase-1 to the IC$_{50}$ concentration for cyclooxygenase-2 is greater than 50.

Selective inhibitors of COX-2 for use in the method herein as inhibitors of expression of HPV protein are described in U.S. Pat. No. 6,486,203, the whole of which is incorporated herein by reference, as well as any selective inhibitors of COX-2 meeting the above recited definition which are not described in U.S. Pat. No. 6,486,203 including NS-398 which is N-[2-(cylohexyloxy)-4-nitrophenyl]-methanesulfonamide. Preferred selective inhibitors of COX-2 for use herein are 3-(phenyl)-4-(4-(methylsulfonyl)phenyl)-2-(5H)-furanone which is sold under the tradename Vioxx™ and 4-[5-(4-methylphenyl)-3-(trifluoromethyl)-1H-pyrazol-1-yl]benzenesulfonamide which is sold under the tradename Celebrex™. Other selective inhibitors of cyclooxygenase-2 useful herein and tested herein include 4-[5-(4-chlorophenyl)-3-trifluoromethyl)-1H-pyrazol-1-yl]benzenesulfonamide, 4-[5-phenyl-3-(trifluoromethyl)-1H-pyrazol-1-yl] benzenesulfonamide, 4-[5-(4-fluorophenyl) -3-(trifluoromethyl)-1H-pyrazol-1-yl]benzenemethylsulfone, 5-bromo-2-(4-fluorophenyl)-3-(4-(methylsulfonyl)phenyl) thiopene, indomethacin heptyl ester and N-(2-phenylethyl)-indomethacin amide. The dosage of selective inhibitor of COX-2 for the method herein is a cyclooxygenase-2 inhibiting amount which is a therapeutically effective amount. In general, the dosage ranges from 0.1 to 30 mg/kg. The dosages for any particular agent will vary within said range. For Celebrex™, the dosage preferably ranges from 3 to 12 mg/kg. For Vioxx™, the dosage preferably ranges from 0.1 to 1 mg/kg. For NS-398, the dosages preferably range from 1 to 100 mg/kg.

We turn now to the case of the inhibitors of HPV protein being diaryl heterocycles. One group of these diaryl heterocycles has the structure

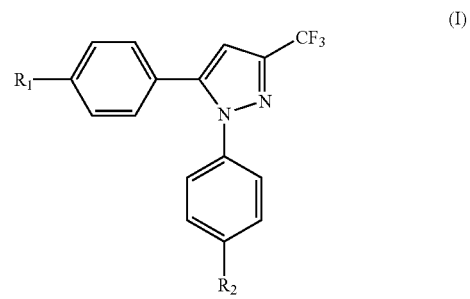

where R$_1$ is C$_1$–C$_6$alkyl, e.g., methyl, halogen, e.g., chlorine or fluorine, or H and R$_2$ is OR where R is C$_1$–C$_6$alkyl, e.g., methoxy, sulfonamide, i.e., SO$_2$NH$_2$, or methyl sulfone. The compounds of the structure (I) include not only selective inhibitors of cyclooxygenase-2, but also selective inhibitors of cyclooxygenase-1 (compounds for which the ratio of IC$_{50}$ concentration for cyclooxygenase-2 to the IC$_{50}$ concentration for cyclooxygenase-1 is greater than 1). Compounds of structure (I) which are selective inhibitors of cyclooxygenase-2 and are members of the class of these described in the paragraph above, include 4-5[-(4-methylphenyl)-3-trifluoromethyl)-1H-pyrazol-1-yl]benzenesulfonamide, which is sold under the trade name Celebrex™, 4-[5-(4-chlorophenyl)-3-(trifluoromethyl)-1H-pyrazol-1-yl]benzenesulfonamide, also known as SC-236, 4-[5-phenyl-3-(trifluoromethyl)-1H-pyrazol-1-yl]benzenesulfonamide, also known as PTPBS and the compound of structure (I) where R$_1$ is fluorine and R$_2$ is methylsulfonyl which is described above as 4-[5-(4-fluorophenyl)-3-(trifluoromethyl)-1H-pyrazol-1-yl]benzenemethylsulfone, also known as SC-58125. Another diaryl heterocycle which is a selective inhibitor of cyclooxygenase-2 which is useful herein and has been tested herein is 5-bromo-2-(4-fluorophenyl)-3-(4-(methylsulfonyl) phenylthiophene, also known as DuP-697. Compounds of the structure (I) where R$_2$ is OR include selective inhibitors of cyclooxygenase-1. A compound of structure (I) where R$_2$ is OCH$_3$ and is a selective inhibitor of cyclooxygenase-1 and which is useful herein and has been tested herein has the structure (I) where R$_1$ is chlorine and R$_2$ is OCH$_3$ and is named 5-(4-chlorophenyl)-1-(4-methoxyphenyl)-3-(trifluoromethyl)-1H-pyrazole and is also known as SC-560. The compounds specifically named in this paragraph are commercially available. The dosage of diaryl heterocycle for the method herein is a HPV protein expression downregulating effective amount which is a therapeutically effective amount. In general, the dosage ranges from 0.1 to 30 mg/kg. The dosage for any particular agent will vary within this range.

We turn now to the case where the inhibitor of the expression of HPV protein for the method herein is from a natural source. The term "natural source" is used herein to mean a plant, marine or animal organism. The inhibitors from a natural source for the method herein include polyphenolic compounds and ursolic acid. The polyphenolic compounds include, for example, curcumin, resveratrol, carnosol, shikonin, caffeic acid phenethylester and epigallocatechin gallate (EGCG). In general, the dosage ranges from 1 to 100 mg/kg. Dosage useful for resveratrol include those set forth in U.S. Pat. No. 6,486,203.

We turn now to the case where the inhibitor of expression of HPV protein is a nonsteroidal anti-inflammatory drug (NSAID) or metabolite thereof. The ones for use herein are those functional to inhibit epidermal growth factor-mediated induction of HPV16 E7 by the testing method set forth in Background Example 6 hereinafter. Suitable nonsteroidal anti-inflammatory drugs and metabolites thereof include sulindac sulfone, sulindac sulfide, naproxen, indomethacin and flufenamic acid. The dosages for use herein include the dosages associated with any other NSAID or NSAID metabolite use.

Inhibitor of expression of HPV protein can be used alone or in combination. A plurality of agents within a class of inhibitors can be used, or a plurality of agents from different classes of inhibitors can be used. For example, ciglitazone or rosiglitazone can be used in combination with Vioxx™ or Celebrex™. Use of two agents together can enable use of a concentration of each agent which is less than the optimum concentration for each agent when used alone to achieve the same expression inhibiting and treatment effect as the optimum concentration of single agent thereby minimizing the risk of side effects compared to when any particular agent is used alone.

Routes of administration include topical, oral and intravenous. Topical administration is preferred in those cases where it is applicable because this route enables high concentration to be delivered locally while avoiding potential systemic side effects. When inhibitor of expression of HPV protein is applied topically, it is preferably applied in a cream or ointment present therein at a concentration of about 0.1 to 10% by weight.

The treatment is continued from day-to-day as long as infection and/or symptoms thereof persist.

The invention is indicated and illustrated by the following background and working examples.

BACKGROUND EXAMPLE 1

Ciglitazone was incubated with CaSki cells (prototypic cervical cancer cells known to be infected with HPV16). The number of CaSki cells was $3 \times 10^6$ in a 10 cm diameter dish. Incubation were carried out for 24 hours with 0, 1, 5, 10 and 20 μM ciglitazone.

Western blotting was carried out to determine levels of HPV16 E7 protein. The Western blot results show suppression by ciglitazone of HPV16 E7 protein. Northern blotting was carried out to determine levels of HPV16 E7 mRNA. The Northern blot results show suppression of HPV16 E7 mRNA by ciglitazone. Nuclear run-off testing was carried out to determine level of gene transcription. The nuclear run-off results show reduction of gene transcription by ciglitazone.

The results show that ciglitazone causes dose dependent reduction of gene transcription (nuclear run-off test) leading to dose dependent reduction in E7 mRNA (Northern blot results) leading to dose dependent inhibition of E7 protein expression (Western blot results).

BACKGROUND EXAMPLE 2

HPV16 upstream regulatory region (URR) ligated to luciferase gene transfected into CaSki cells is incubated for 24 hours with ciglitazone and with 15d-PGJ$_2$ (in each case, concentration of 0 μM, 5 μM, 10 μM, 15 μM, 20 μM and 25 μM). The results are shown in FIG. 1 and are that ciglitazone and 15d-PGJ$_2$ cause dose dependent inhibition of the upstream regulatory region of HPV16 in CaSki cells, i.e., they shut down the promoter for HPV16 and are consistent with the results shown in the nuclear run-off test of Background Example 1. Note that cells contain endogenous activator that drives expression of E7, and ciglitazone and 15d-PGJ$_2$ are shown to inhibit the activation.

BACKGROUND EXAMPLE 3

NS-398 at concentrations of 0, 10, 20, 40, 60, 100, 250 and 500 μM was incubated with CaSki cells ($3 \times 10^6$ in a 10 cm diameter dish) for 24 hours.

Northern blotting was carried out to determine HPV16 E7 mRNA levels in each case.

The data shows dose dependent suppression by NS-398 of HPV E7 mRNA levels meaning that mRNA expression is inhibited by incubations with NS-398 in a dose-dependent relation.

Celebrex™ at concentrations of 0, 0.1, 0.25, 0.5, 1.0, 2.5 and 5.0 μM was incubated with CaSki cell ($3.0 \times 10^6$ in a 10 cm diameter dish) for 24 hours. Western blotting was carried out to determine levels of HPV16 E7 protein; the results show dose dependent suppression by Celebrex™ of HPV16 E7 protein. Northern blotting was carried out to determine levels of HPV16 E6 mRNA; the results show dose dependent suppression of HPV16 E6 mRNA by Celebrex™.

SC-236, also know as 4-[5-(4-chlorophenyl)-3-trifluoromethyl)-1H-pyrazol-1-yl]benzenesulfonamide, at concentrations of 0, 0.1, 0.5, 1.0, 2.5 and 5.0 μM was incubated with CaSki cells ($3.0 \times 10^6$ in a 10 cm diameter disk) for 24 hours. Western blotting was carried out to determine levels of HPV16 E7 protein; the results show dose dependent suppression by SC-236 of HPV16 E7 protein. Northern blotting was carried out to determine levels of HPV16 E6 mRNA; the results show dose dependent suppression of HPV16 E6 mRNA by SC-236.

Indomethacin heptyl ester (Catalog No. 70271 from Cayman Chemical) at concentrations of 0, 0.1, 0.5, 1.0, 2.5 and 5.0 μM was incubated with CaSki cells ($3.0 \times 10^6$ in a 10 cm diameter dish) for 24 hours. Western blotting was carried out to determine levels of HPV16 E7 protein; the results show dose dependent suppression by indomethacin heptyl ester of HPV16 E7 protein. Northern blotting was carried out to determine levels of HPV16 E6 mRNA; the results show dose dependent suppression by indomethacin heptyl ester of HPV16 E6 mRNA.

N-(2-phenylethyl)-indomethacin amide (Catalog No. 70272 from Cayman Chemical) at concentrations of 0, 0.1, 0.25, and 1.0 μM was incubated with CaSki cells ($3.0 \times 10^6$ in a 10 cm diameter dish) for 24 hours. Western blotting was carried out to determine levels of HPV16 E7 protein; the results show dose dependent suppression by N-(2-phenylethyl)-indomethacin amide of HPV16 E7 protein. Northern blotting was carried out to determine levels of HPV16 E6 mRNA; the results show dose dependent suppression by N-(2-phenylethyl)-indomethacin amide of HPV16 E6 mRNA.

DuP-697 (from Calbiochem) also known as 5-bromo-2-(4-fluorophenyl)-3-(4-(methylsulfonyl)phenyl)thiophene at concentrations of 0, 0.5 and 1.0 μM was incubated with CaSki cells ($3.0 \times 10^6$ in a 10 cm diameter dish) for 24 hours. Western blotting was carried out to determine levels of HPV16 E7 protein; the results show suppression by DuP-697 of HPV16 E7 protein. Northern blotting was carried to determine levels of HPV 16 E6 mRNA; the results show suppression of HPV16 E6 mRNA by DuP-697.

4-[5-Phenyl-3-(trifluoromethyl)-1H-pyrazol-1-yl]benzenesulfonamide at concentrations of 0, 0.5 and 1.0 µM was incubated with CaSki cells ($3.0 \times 10^6$ in a 10 cm diameter dish) for 24 hours. Western blotting was carried to determine levels of HPV16 E7 protein; the results show suppression by 4-[5-phenyl-3-(trifluoromethyl)-1H-pyrazol-1-yl]benzenesulfonamide of HPV16 E7 protein. Northern blotting was carried to determine levels of HPV 16 E6 mRNA; the results show suppression of HPV16 E6 mRNA by 4-[5-phenyl-3-(trifluoromethyl)-1H-pyrazol-1-yl]benzenesulfonamide.

SC-58125, described above, at concentrations of 0, 0.5 and 1.0 µM was incubated with CaSki cells ($3.0 \times 10^6$ in a 10 cm diameter dish) for 24 hours. Western blotting was carried to determine levels of HPV16 E7 protein; the results show suppression by SC-58125 of HPV16 E7 protein. Northern blotting was carried to determine levels of HPV 16 E6 mRNA; the results show suppression of HPV16 E6 mRNA by SC-58125.

SC-560, described above, at concentrations of 0, 0.5 and 1.0 µM was incubated with CaSki cells ($3.0 \times 10^6$ in a 10 cm diameter dish) for 24 hours. Western blotting was carried to determine levels of HPV16 E7 protein; the results show suppression by SC-560 of HPV16 E7 protein. Northern blotting was carried to determine levels of HPV 16 E6 mRNA; the results show suppression of HPV16 E6 mRNA by SC-560.

BACKGROUND EXAMPLE 4

Epidermal growth factor (EGF) at 10 nanograms/ml was added to CaSki cells ($3 \times 10^6$ in a 10 cm diameter dish) together with 0, or 5 µM or 10 µM or 15 µM ciglitazone and incubation is carried out for 24 hours.

Western blot testing was carried out for HPV16 E7 protein.

The results showed ciglitazone causes dose dependent inhibition of EGF-mediated induction and thereby inhibition of E7 protein expression even with EGF being present.

BACKGROUND EXAMPLE 5

Epidermal growth factor at 10 nanograms/ml was added to CaSki cells ($3 \times 10^6$ in a 10 cm diameter dish) together with 50 µM sulindac sulfide or 100 µM sulindac sulfide or 15 µM ciglitazone or 15 µM 15d-$PGJ_2$.

Northern blot testing was carried out for HPV16 E7 mRNA.

The results show inhibition of EGF-mediated induction of HPV16 E7 mRNA by the PPARγ ligands ciglitazone and 15d-$PGJ_2$ and for sulindac sulfide.

BACKGROUND EXAMPLE 6

Epidermal growth factor (EGF) at 10 nanograms/ml was incubated with CaSki cells ($3 \times 10^6$ in a 10 cm diameter dish) and 100 µM ibuprofen, 100 µM piroxicam, 100 µM S-naproxen, 100 µM aspirin, 100 µM sulindac sulfone, 100 µM sulindac sulfide, 100 µM naproxen, 100 µM indomethacin, 100 µM flufenamic acid and for comparison purposes 25 µM 15d-$PGJ_2$.

Northern blot testing was carried out for HPV16 E7 mRNA.

The results show inhibition of EGF-mediated induction of HPV16 E7 by sulindac sulfide, sulindac sulfone, indomethacin, naproxen, flufenamic acid and 15d-$PGJ_2$ but not by piroxicam, S-naproxen, aspirin and ibuprofen.

BACKGROUND EXAMPLE 7

Curcumin (5 µM), resveratrol (15 µM), ciglitazone (20 µM) or 15d-$PGJ_2$ (15 µM) were incubated with CaSki cells ($3 \times 10^6$ in a 10 cm diameter dish) for 24 hours.

Northern blot testing was carried our for HPV16 E6 mRNA.

The results showed that in all four cases, two with the polyphenols curcumin and resveratrol and two with the PPARγ ligands ciglitazone and 15d-$PGJ_2$, there was down-regulation of E6 mRNA in the CaSki cervical cancer cell line.

EXAMPLE I

A 43-year-old male presents to a dermatologist for evaluation of multiple perianal warts. A diagnosis of condylomata acuminata is made. A representative lesion is biopsied and HPV11 is detected. The patient is treated with rosiglitazone 4 mg orally twice each day for 8 weeks. The patient is reevaluated by the dermatologist 8 weeks later. The perianal warts are no longer detectable and the medication is discontinued.

EXAMPLE II

A 29-year-old woman presents to her gynecologist for evaluation. A routine pap test reveals highly atypical squamous cells. On biopsy, the patient is found to have cervical intraepithelial neoplasia. HPV16 is detected. Treatment with Vioxx™ 25 mg orally each day is begun and given for six months. At the end of six months, the patient undergoes repeat biopsy and there is no further evidence of cervical intraepithelial neoplasia. The Vioxx™ is discontinued with no recurrence of cervical intraepithelial neoplasia.

When 25 mg orally each day of SC-560 is substituted for the Vioxx™, there is no evidence of cervical intraepithelial neoplasia and no recurrence after discontinuance of the drug.

EXAMPLE III

A 42-year-old woman seeks gynecologic evaluation because of pelvic pain. On pelvic examination, a cervical mass is detected. Biopsy of the cervical mass reveals poorly differentiated squamous cell carcinoma. A CAT scan of the pelvis is done and reveals a cervical mass as well as a question of enlarged pelvic lymph nodes. The patient undergoes a hysterectomy along with resection of regional lymph nodes. Pathological evaluation indicates that the cervical cancer has metastasized to local lymph nodes. HPV16 is detected. The patient is treated with a course of radiation therapy plus indomethacin 50 mg orally three times a day for 12 months. A repeat CAT scan is done and reveals no evidence of disease. The indomethacin is discontinued.

EXAMPLE IV

A 14-year-old girl presents to a local dermatologist because of small cutaneous growths on the hand. A diagnosis of HPV mediated cutaneous warts is made. The patient is instructed to apply an ointment containing 5% rosiglitazone to the affected areas twice a day. The warts gradually disappear and after three months are no longer detectable.

The same results occur with an ointment containing 5% resveratrol instead of the ointment containing rosiglitazone.

Variations

Many variations of the above will be obvious to those skilled in the art. Therefore, the invention is defined in the claims.

What is claimed is:

1. A method for treating a patient infected with HPV16 and as a result having cervical intraepithelial neoplasia or cervical cancer comprising orally administering to said patient a therapeutically effective amount of down regulator of the expression of HPV protein of HPV16 where said down regulator comprises a selective inhibitor of COX-2, and where the HPV protein comprises E6 protein and where the administering is for a period up to 6 months.

2. The method of claim 1 where the selective inhibitor of COX-2 comprises 3-(phenyl)-4-(4-methyl sulfonyl) phenyl-2-(5h)furanone.

3. The method of claim 1 where the selective inhibitor of COX-2 is 4-[5-(4-methylphenyl)-3-(trifluoromethyl)-1H-pyrazol-1-yl]benzenesulfonamide.

* * * * *